(12) United States Patent
Ying et al.

(10) Patent No.: US 12,168,689 B2
(45) Date of Patent: Dec. 17, 2024

(54) IgG1 FC MONOMER AND APPLICATION THEREOF

(71) Applicant: Suzhou Forlong Biotechnology Co., Ltd., Jiangsu (CN)

(72) Inventors: Tianlei Ying, Shanghai (CN); Chunyu Wang, Shanghai (CN)

(73) Assignee: Suzhou Forlong Biotechnology Co., Ltd., Jiangsu (CN)

( * ) Notice: Subject to any disclaimer, the term of this patent is extended or adjusted under 35 U.S.C. 154(b) by 0 days.

(21) Appl. No.: 16/759,083

(22) PCT Filed: Oct. 24, 2018

(86) PCT No.: PCT/CN2018/111577
§ 371 (c)(1),
(2) Date: Apr. 24, 2020

(87) PCT Pub. No.: WO2019/080858
PCT Pub. Date: May 2, 2019

(65) Prior Publication Data
US 2021/0206847 A1    Jul. 8, 2021

(30) Foreign Application Priority Data

Oct. 26, 2017 (CN) .......................... 201711014953.3

(51) Int. Cl.
| C07K 16/28 | (2006.01) |
| C07K 16/08 | (2006.01) |
| C07K 16/12 | (2006.01) |
| C07K 16/30 | (2006.01) |
| C12N 15/63 | (2006.01) |
| C40B 40/10 | (2006.01) |
| A61P 35/00 | (2006.01) |

(52) U.S. Cl.
CPC ............ *C07K 16/283* (2013.01); *C07K 16/08* (2013.01); *C07K 16/12* (2013.01); *C07K 16/30* (2013.01); *C12N 15/63* (2013.01); *C40B 40/10* (2013.01); *A61P 35/00* (2018.01); *C07K 2317/524* (2013.01); *C07K 2317/526* (2013.01); *C07K 2317/565* (2013.01); *C07K 2319/55* (2013.01)

(58) Field of Classification Search
CPC ...... C07K 16/283; C07K 16/08; C07K 16/12; C07K 16/30; C07K 2317/524; C07K 2317/526; A61P 35/00
See application file for complete search history.

(56) References Cited

U.S. PATENT DOCUMENTS

| 9,676,857 B2 * | 6/2017 | Dimitrov | ............. G01N 33/544 |
| 10,000,576 B1 * | 6/2018 | Weisser | ................. A61K 45/06 |
| 2006/0074225 A1 * | 4/2006 | Chamberlain | ......... C07K 16/44 |
| | | | 530/387.1 |
| 2012/0244578 A1 | 9/2012 | Kannan et al. | |
| 2013/0177555 A1 | 7/2013 | Wilkinson et al. | |
| 2015/0050278 A1 * | 2/2015 | Dimitrov | ............. G01N 33/573 |
| | | | 424/134.1 |
| 2015/0353636 A1 | 12/2015 | Parren et al. | |
| 2018/0118828 A1 | 5/2018 | Bernett | |
| 2021/0206847 A1 | 7/2021 | Ying | |

FOREIGN PATENT DOCUMENTS

| CN | 105229026 A | 1/2016 |
| CN | 106380521 A | 2/2017 |
| CN | 106659775   | 5/2017 |
| CN | 107880136 A | 4/2018 |
| CN | 108101988   | 6/2018 |
| CN | 109468278   | 3/2019 |
| CN | 109503718   | 3/2019 |
| CN | 109705211   | 5/2019 |
| CN | 110551223   | 12/2019 |
| CN | 111132733 A | 5/2020 |

(Continued)

OTHER PUBLICATIONS

Ferrara et al., PNAS (2011), vol. 108, No. 31, pp. 12669-12674. (Year: 2011).*
Borrock, M. J.: "Chain A, Ig Gamma-1 Chain C Region", PD: 3S7G_A, 227aa Linear Oct. 10, 2012, 1-2.
Ferrara, C. et al.: "Chain A, Human Fc Fragment", PDB: 3SGJ_A. 225aa Linear, (Oct. 10,2012) pp. 1-2.
Holliger P, et al.: "Engineered Antibodies Fragments and the Rise of Siingle Domains" , Nat: Biotechnol, 2005, 23 (9): 1126-1136.
International Search Report Application PCT/CN2018/111577; Dated Jan. 29, 2019; pp. 8.
Lu, J., et al.: "Chain A. Ig Comma-1 Chain C Region", PDB: 4X4M_A, 219aa Linear (NCBI Genbank), Apr. 8, 2015 1-2.

(Continued)

*Primary Examiner* — Meera Natarajan
*Assistant Examiner* — Cheom-Gil Cheong
(74) *Attorney, Agent, or Firm* — Ice Miller LLP

(57) ABSTRACT

An IgG1 Fc monomer, a preparation method therefor and an application thereof. Causing an Fc dimer of a novel IgG1 Fc monomer sequence for which an antibody IgG1 constant region is modified to become an Fc monomer by means of the modification on a human antibody IgG1 constant region Fc that uses antibody engineering technology, and maintaining an FcRn binding function; the present application has the feature of very low non-specific binding with unrelated proteins, and the main features of the Fc monomer comprise the T366, L368, P395, and K409 positions in a CH3 region of the constant region of the antibody having mutations, and the monomer being highly efficiently expressed in prokaryotic cells; the monomer may bind to FcRn by using a pH-dependent specific binding mode, and has the feature of very low non-specific binding. By using said Fc monomer, the same may be fused or coupled with various proteins, polypeptides, small molecules, nucleic acids and the like for different targets such that the fused or coupled molecules have the feature of being capable of binding to FcRn by using pH dependence.

13 Claims, 2 Drawing Sheets
Specification includes a Sequence Listing.

(56) References Cited

FOREIGN PATENT DOCUMENTS

| | | |
|---|---|---|
| CN | 111303296 | 6/2020 |
| CN | 111699200 | 9/2020 |
| CN | 111741977 | 10/2020 |
| CN | 112105645 A | 12/2020 |
| CN | 112584851 | 3/2021 |
| CN | 113185600 | 7/2021 |
| JP | 2013511281 A | 4/2013 |
| JP | 2013537416 A | 10/2013 |
| WO | 2005085282 | 9/2005 |
| WO | 2013138643 A1 | 9/2013 |
| WO | 2016004060 | 1/2016 |
| WO | 2016008973 A1 | 1/2016 |
| WO | 2016095642 A1 | 6/2016 |
| WO | 2019126464 | 6/2019 |
| WO | 2019204665 | 10/2019 |
| WO | 2019213517 | 11/2019 |
| WO | 2020232427 | 11/2020 |
| WO | 2021030688 | 2/2021 |
| WO | 2022247778 | 12/2022 |

OTHER PUBLICATIONS

Matsumiya, S. et al.: "Chain A, Ig Gamma-1 Chain C. Region" PDB: 2DTS_A, 223aa Linear (NCBI Genbank), Oct. 10, 2012 1-2.
Saerens D, et al.: Single-Domain Antibodies as Building Blocks for Novel Therapeutics. Curr Opin Pharmacol. 2008, 8 (5): 600-608.
Silva-Martin, N. et al."Chain A, Ig Gamma-1 Chain C Region" PDB: 4CDH_A, 255aa Linear (NCBI Genbank), Feb. 25, 2015, 1-2.
Wang, X. et al.i.: "IgG Fc Engineering to Modulate Antibody Effector Functions, (protein Cell)", Oct. 6, 2017, 63-73.
Ying, T. et al.: Soluble Monomeric IgG1 Fc, J Biol Chem, 2012, 287 (23): 19399-19408.
Ying, T.: "Monomeric IgG1 Fc Molecules Displaying Unique Fc Receptor Interactions that are Exploitable to Treat Inflammation-Mediated Diseases", MAbs, 2014, 6(5): 1201-1210.
European Search Report for European Application No. 18870768.1; Application Filing Date Oct. 24, 2018; Date of Mailing May 26, 2021 (9 pages).
Office Action for Chinese Application No. 201711014953.3; Application Filing Date Oct. 26, 2017; Date of Mailing Mar. 25, 2020 (13 pages).
Office Action for Japanese Application No. 2020-541849; Application Filing Date Oct. 24, 2018; Date of Mailing May 11, 2021 (14 pages).
Avi Ashkenazi et al. "Immunoadhesins as research tools and therapeutic agents," Current Opinion in Immunology, vol. 9, issue 2 (Apr. 1997) pp. 195-200.
Burvenich Ingrid J G, et al, "Cross-species analysis of Fc engineered anti-Lewis-Y human IgG1 variants in human neonatal receptor transgenic mice reveal importance of S254 and Y436 in binding human neonatal Fc receptor", MAbs 2016, 12 pages.
Chunyu Wang et al. "Engineered Soluble Monomeric IgG1 Fc with Significantly Decreased Non-Specific Binding," Frontiers in Immunology, vol. 8, article 1545 (Nov. 2017) pp. 1-8.

Frederick M. Ausubel et al. "Short Protocols in Molecular Biology. A Compendium of Methods from Current Protocols in Molecular Biology," Current Protocols in Molecular Biology (Jun. 1991).
Giri, J. G. et al. "Utilization of the beta and gamma chains of the IL-2 receptor by the novel cytokine IL-15," The Embo Journal, vol. 13, issue 12 (Jun. 1, 1994) pp. 2822-2830.
Han Kai-ping, et al., "IL-15:IL-15 receptor alpha superagonist complex: High-level co-expression in recombinant mammalian cells, purification and characterization," Cytokine, vol. 56, No. 3, pp. 804-809, Oct. 22, 2011.
Han Kai-ping, et al., "IL-15:IL-15 receptor alpha superagonist complex: High-level co-expression in recombinant mammalian cells, purification and characterization," Cytokine, vol. 56, No. 3, pp. 805-809, Oct. 22, 2011.
International Search Report and Written Opinion issued in App. No. PCT/CN2018/111577, dated Jan. 29, 2019, 11 pages.
International Search Report and Written Opinion issued in App. No. PCT/CN2020/141250, dated Jul. 30, 2021, 7 pages.
International Search Report and Written Opinion issued in App. No. PCT/CN2021/076670, dated Sep. 1, 2021, 9 pages.
International Search Report issued Sep. 1, 2021 in PCT/CN2021/076670, 14 pages.
Jinghe Huang et al. "Broad and potent HIV-1 neutralization by a human antibody that binds the gp41-gp120 interfac," Nature, vol. 515, issue 7525 (Nov. 6, 2014) pp. 138-142.
R.J. Massey "Catalytic antibodies catching on," Nature, vol. 328 (1987) pp. 457-458.
Steven M. Chamow et al. "Immunoadhesins: principles and applications," Trends in Biotechnology, vol. 14, issue 2 (Feb. 1996) pp. 52-60.
Tianlei Ying et al. "Exceptionally potent neutralization of Middle East respiratory syndrome coronavirus by human monoclonal antibodies," Journal of Virology, vol. 88, issue 14 (Apr. 2014) pp. 7796-7805.
Traxlmayr Michael W. et al., "Construction of a Stability Landscape of the CH3 Domain of Human IgG1 by Combining Directed Evolution with High Throughput Sequencing", Journal of Molecular Biology, (Oct. 2012), vol. 423, No. 3, , pp. 397-412.
Xu Wenxin, et al., "Efficacy and Mechanism-of-Action of a Novel Superagonist Interleukin-15: Interleukin-15 Receptor aSu/Fe Fusion complex in Syngeneic Murine Models of Multiple Myeloma," Cancer Research, vol. 73, No. 10, pp. 3077-3082, May 3, 2013.
Xu Wenxin, et al., "Efficacy and Mechanism-of-Action of a Novel Superagonist Interleukin-15: Interleukin-15 Receptor aSu/Fe Fusion complex in Syngeneic Murine Models of Multiple Myeloma," Cancer Research, vol. 73, No. 10, pp. 3077-3086, May 3, 2013.
Yu Deling, et al. "Advances in the Fc function and engineering modification of therapeutic monoclonal antibody", Chinese Journal of Histochemistry and Cytochemistry, (20191231), vol. 28, No. 6, pp. 552-559.
Grabstein, Kenneth H. et al. "Cloning of a T Cell Growth Factor that Interacts with the β Chain of the Interleukin-2 Receptor," Science, vol. 264, issue 5161 (1994) pp. 965-968.

* cited by examiner

IgG1 FC MONOMER AND APPLICATION THEREOF

CROSS REFERENCE TO RELATED APPLICATION

This application is a National Phase of PCT Application No. PCT/CN2018/111577 filed Oct. 24, 2018 which claims priority to Chinese Application No. 201711014953.3 filed on Oct. 26, 2017, entitled "Igg1 Fc Monomer and Application Thereof", which is incorporated herein by reference in its entirety.

SEQUENCE LISTING

A Sequence Listing, incorporated herein by reference, is submitted in electronic form as an ASCII text file, created Oct. 21, 2020 and Jan. 13, 2021, having size 8.0 Kb, and named "8MX3800.txt".

TECHNICAL FIELD

The application relates to the technical field of biology, and particularly an IgG1 Fc monomer, a preparation method thereof and an application thereof.

BACKGROUND

Research shows that there are mainly three long-acting technologies of the current protein drug: PEG (polyethylene glycol) modification technology, HSA (human serum albumin) fusion technology and Fc (human antibody Fc region) fusion technology, which have their own weaknesses respectively, wherein a common key disadvantage is that there is a significant increase in the molecular weight of the fused or modified protein drug, and a significantly decrease in the yield and clinical efficacy of the fused protein drug, for example, human antibody constant region Fc is a homodimer, which has a molecular weight of 60 kDa, and the fusion protein can only be in the dimerized form, which tends to increase the molecular weight of the fusion protein by several times, and meanwhile the dimerized drug molecules may interfere with one another to affect the drug effect. For a long time, researchers have been exploring the use of "antibody fragment" with a smaller molecular weight and soluble expression in prokaryotic cells, as a new generation of antibody drugs with low production costs and strong tissue penetration capabilities. The antibody fragment includes Fab, single-chain antibody (scFv), nanobody, and the like. In order to reduce molecular weight, the antibody fragments need to discard the Fc region of IgG so that they cannot bind to FcRn, resulting in an extremely short half-life (within two hours) in vivo so that it is difficult for the current small molecular weight antibody fragment to be truly applied to clinical treatment of diseases as drugs.

The prior art discloses that the Fc region of human IgG is a homodimer. In the early study of the application, the human IgG1 Fc region is modified by using a novel method of multi-functional screening, and one billion ($10^9$) different Fc mutant molecules are screened for druggability and FcRn binding activity, etc., an Fc monomer molecule (mFc) is constructed, which has a molecular weight only half that of the IgG1 Fc region. It completely reserves the FcRn binding property and Protein A/G binding property of the antibody Fc region, and has an excellent property of highly soluble expression in E. coli, the half-life can reach about two days in the animal body; during the research, it is found that it has a very strong non-specific binding property, which may make mFc non-specifically bind to unrelated proteins when used in vivo, greatly limiting its clinical use scope. Therefore, based on the previous research, the present application changes mutation sites and optimizes a screening step (as shown in FIG. 1), obtaining a novel IgG1 Fc monomer and sFc (small-sized Fc) which not only maintains the excellent properties of the previous Fc monomer, but significantly improves non-specific binding property.

The prior art related to the present application is as follows:
[1] HOLLIGER P, HUDSON P J Engineered antibodies fragments and the rise of single domains [J]. Nat: Biotechnol, 2005, 23 (9): 1126-1136.
[2] SAERENS D, GHASSABEH G H, MUYLDERMANS S. Single-domain antibodies as building blocks for novel therapeutics [J]. Curr Opin Pharmacol. 2008, 8 (5): 600-608.
[3] YING T, FENG Y, WANG Y, et al. Monomeric IgG1 Fc molecules displaying unique Fc receptor interactions that are exploitable to treat inflammation-mediated diseases [J]. MAbs, 2014, 6(5): 1201-1210.
[4] YING T. CHEN W, GONG R, et al. Soluble monomeric IgG1 Fc [J]. J Biol Chem, 2012, 287 (23): 19399-19408.

SUMMARY

The purpose of the present application is to provide a novel IgG1 Fc monomer having low non-specificity subjected to antibody engineering modification based on the existing technology, and specifically relate to an IgG1 Fc monomer and the application thereof.

Specifically, the present application discloses nucleic acids encoding the IgG1 Fc monomer; some embodiments disclose vectors comprising the nucleic acids, and host cells comprising these vectors.

The IgG1 constant region Fc is a homodimer, it can bind to FcRn (neonatal Fc receptor) with a special pH-dependent binding mode, so that IgG1 has a longer half-life in vivo; the present application is directed to the novel IgG1 Fc monomer sequence after an antibody IgG1 constant region is modified; an Fc dimer becomes an Fc monomer by modification of the human antibody IgG1 constant region Fc using antibody engineering technology, thus maintaining an FcRn binding function and having the feature of very low non-specific binding to unrelated proteins, and the main features of the Fc monomer lie in that the T366, L368, P395, and K409 positions in a CH3 region of the antibody constant region have mutations, and the monomer is highly efficiently expressed in prokaryotic cells; the monomer may bind to FcRn by using a pH-dependent specific binding mode, and has the feature of very low non-specific binding.

Said novel Fc monomer prepared according to the present application may be fused or coupled with various proteins, polypeptides, small molecules, nucleic acids and the like for different targets such that the fused or coupled molecules have the feature of being capable of binding to FcRn by using pH dependence.

The objective of the present application is achieved by the following technical solutions:
1. Screening and Judgment of a Novel IgG1 Fc Monomer (sFc) (as Shown in FIG. 1)

In the present application, mutations are performed in the IgG1 constant region and comprise four specific mutation sites and one random mutation site (Leu-351, Thr-366, Leu-368, Pro-395, Lys-409) involved in monomer formation, and further comprise two random mutation sites (Met- 428, Asn-434) related to FcRn binding, based on which an IgG1 Fc mutant antibody library with a library capacity of $1.28 \times 10^5$ is constructed.

A novel IgG1 Fc monomer is screened by biotin-labeled soluble FcRn protein. Biotin-labeled soluble FcRn is immobilized on streptavidin-coated magnetic beads. $10^{12}$ phages displayed Fc at room temperature is incubated with protein G at 1st, 2nd round; and respectively incubated with 5, 4, 2 micrograms of FcRn antigen for two hours at 3rd, 4th, and 5th rounds, $10^{12}$ phages are used for each round of screening, and polyclonal phage ELISA is used to detect enrichment of antibodies. Phages and coated proteins are incubated at the 3rd, 4th, and 5th round, and phage-protein binding is detected with anti-phage HRP-coupled antibodies. Based on polyclonal phage ELISA results, a very significant enrichment is obtained after 4th and 5th round of screening.

In the present application, the phages obtained from these two rounds of screening are used to infect TG1 cells, randomly selecting clones for performing monoclonal phage ELISA, thus further sequencing to identify the enriched IgG1 Fc, and SEC is used to perform monomer judgment. The results are shown in FIG. 1, sFc and another screened protein 1-B10-9 (M428L mutation additionally occurs compared with sFc) are monomers.

2. Novel IgG1 Fc Monomer (sFc) Stability Test

In the present application, sFc, 1-B10-9, mFc and Fc are respectively diluted at a concentration of 0.25 mg/ml, and the stability of the proteins is detected at 216 nm by using the instrument Jasco J-815 spectropolarimeter (Jasco International), and the results are shown in FIG. 2: the Tm values of sFc, 1-B10-9, mFc and Fc are: 62.4±0.1° C., 64.0±0.1° C., 58.4±0.2° C., 80.6±0.3° C.

3. Binding Capacity of the Novel IgG1 Fc Monomer (sFc) to FcRn by Using Surface Plasmon Resonance (SPR) Detection In the present application, SA (biotin avidin) chip is used to detect the binding capacity of the novel IgG1 Fc monomer to FcRn, wherein the soluble expression preparation of the novel IgG1 Fc monomer is carried out basically based on the literature. During the detection process, the protein is diluted based on a two-fold ratio (IgG1 Fc dilution 200 nM to 6.25 nM, IgG1 Fc monomer dilution 400 nM to 12.5 nM), the affinity constant is detected by detecting binding and dissociation at pH 6.0, and the results are shown in FIG. 3: the binding capacity to FcRn of the novel IgG1 Fc monomers sFc or 1-B10-9 remains substantially consistent as compared to Fc or mFc.

4. Non-Specific Binding Detection of the Novel IgG1 Fc Monomer (sFc)

In the present application, Fc is eukaryotically expressed, mFc and the novel IgG1 Fc monomer sFc are prokaryotically expressed, followed by Protein G purification, and then viruses and cancer-related proteins (gp140, mesothelin, ZIKV EDII, ZIKV EDIII, 5T4, PD-L1, OX40, TIM-3) are used to coat plate (#3690) with 100 ng per well at 4° C. overnight, 100 μl of 3% MPBS (PBS+3% milk) is added into each well, blocking at 37° C. for 1 h, then 0.05% PBST (PBS+0.05% Tween 20) is used for washing, Fc, mFc, novel IgG1 Fc monomer sFc and 1-B10-9 are diluted by 3-fold dilution from 2 μM, incubated with the antigen for 1.5 h at 37° C., washed with 0.05% PBST and added with 1:1000 anti-FLAG-HRP and incubated for 45 minutes at 37° C., and ABTS is added to develop a color at an absorbance of 405 nm. Comparing their non-specific binding capability, the novel IgG1 Fc monomer is significantly more excellent than mFc. The ELISA results shown in FIG. 4 are that the novel IgG1 Fc monomer sFc and 1-B10-9 have a low non-specific binding.

In the present application, the peptide chain of IgG1 Fc monomer comprises CH2 and CH3 domains, wherein the peptide chain comprises an amino acid sequence of SEQ ID NO: 1, X1 is R/T; X2 is L/H; X3 is P/K; X4 is K/T, and Fc is a monomer and capable of binding to a neonatal Fc receptor (FcRn).

The IgG1 Fc monomer peptide comprises an amino acid sequence of SEQ ID NO: 2, wherein X1 is R; X2 is H; X3 is K; X4 is T.

In the present application, the CH3 domain comprises:
(a) amino acid sites 341-447 in the amino acid sequence listed in SEQ ID NO: 1; and/or
(b) amino acid sites 341-447 in the amino acid sequence listed in SEQ ID NO: 2;

The present application provides a fusion protein comprising the above-mentioned IgG1 Fc monomer polypeptide, or the CH3 domain, and a heterologous protein;

The heterologous protein comprises a heavy chain variable region and a light chain variable region, and can specifically bind to an antigen of interest; the heterologous protein described in the embodiment of the present application is an antigen derived from a pathogen; the pathogen is a virus or a bacterium, wherein the virus is selected from human immunodeficiency virus (HIV);

The heterologous protein is also selected from a tumor antigen; wherein the tumor is leukemia, lymphoma, multiple myeloma, malignant melanoma, breast cancer, lung cancer, liver cancer, pancreatic cancer, prostate cancer, colon cancer or renal cell carcinoma.

The heterologous protein is further selected from an autoimmune or inflammatory disease antigen.

The fusion protein of the present application comprises a toxin;

In the fusion protein of the present application, the heterologous protein is selected from a cytokine, a soluble receptor, a growth factor or a label.

In the fusion protein of the present application, the heterologous protein is further selected from a human interferon, an erythropoietin, a soluble tumor necrosis factor receptor, CTLA-4, a soluble IL-4 receptor or a factor IX.

The application also provides a nucleic acid molecule encoding the IgG1 Fc monomer polypeptide, the CH3 domain, and/or the fusion protein.

The application also provides a plasmid comprising the nucleic acid molecule.

The application also provides a host cell comprising the plasmid.

The present application also provides a pharmaceutical composition comprising an effective preventive/therapeutic dose of the IgG1 Fc monomer polypeptide, the CH3 domain, or the fusion protein, and a pharmaceutically acceptable carrier.

The application also provides a pharmaceutical composition comprising an effective preventive/therapeutic dose of the nucleic acid molecule or the plasmid, and a pharmaceutically acceptable carrier.

The present application also provides a medicinal composition comprising an effective preventive/therapeutic dose of the IgG1 Fc monomer Fc polypeptide, the CH3 domain, and/or the fusion protein, coupled to a detectable label; wherein the detectable label is a fluorescent label, a radioactive label, an avidin, a biotin, or an enzyme.

The present application also provides a method for treating an autoimmune disease, an inflammatory disease, a neurodegenerative disease, a cancer or a pathogen infection, comprising administering an effective therapeutic dose of the fusion protein, the nucleic acid molecule, or the plasmid to a subject; wherein the subject has been infected with a pathogen, wherein the fusion protein can specifically bind to the pathogen, and wherein the method is used to treat the pathogen in the infected subject, wherein the pathogen is a virus, particularly an immunodeficiency virus.

The application also provides a method for constructing a recombinant monomeric Fc library, comprising:
(a) introducing a mutation into one or more beta chains of the CH2 or CH3 domain of the IgG1 Fc monomer polypeptide; or
(b) replacing a part of the CH2 domain or the CH3 domain with a complementary determining region (CDR) or a functional fragment of a specific binding antigen retained in a heterologous immunoglobulin variable region; or
(c) both;
using the above method to build a library.

The recombinant monomeric Fc library according to the above method comprises CH2 and CH3 domains, and each IgG1 Fc monomer polypeptide in the library:
(a) being in a monomeric form;
(b) having a molecular weight less than 30 kDa;
(c) being capable of binding to neonatal Fc receptors (FcRn);
(d) comprising an amino acid sequence that is at least 95% identical to SEQ ID NO: 1.

In the present application, a library of nucleic acid molecule-encoding monomeric Fc polypeptide comprises CH2 and CH3 domains, and each Fc polypeptide encoded in the library:
(a) being a monomer;
(b) having a molecular weight less than 30 kDa;
(c) being capable of binding to FcRn;
(d) comprising an amino acid sequence that is at least 95% identical to SEQ ID NO: 1.

The novel IgG1 Fc monomer (sFc) provided by the present application can be used as a small-molecular-weight long-acting monomer module and fused with an antibody fragment to construct a novel genetic engineering antibody, which provides an important theoretical basis and solution for breaking through the bottleneck of the development of antibody drugs; or it can be fused or coupled with various proteins, peptides, small molecules, nucleic acids, etc. for different targets, so that the fused or coupled molecules have the characteristics of binding to FcRn by using pH dependence, which has a potentially better druggability and a longer half-life in vivo.

DETAILED DESCRIPTION

Example 1

Figure 1:
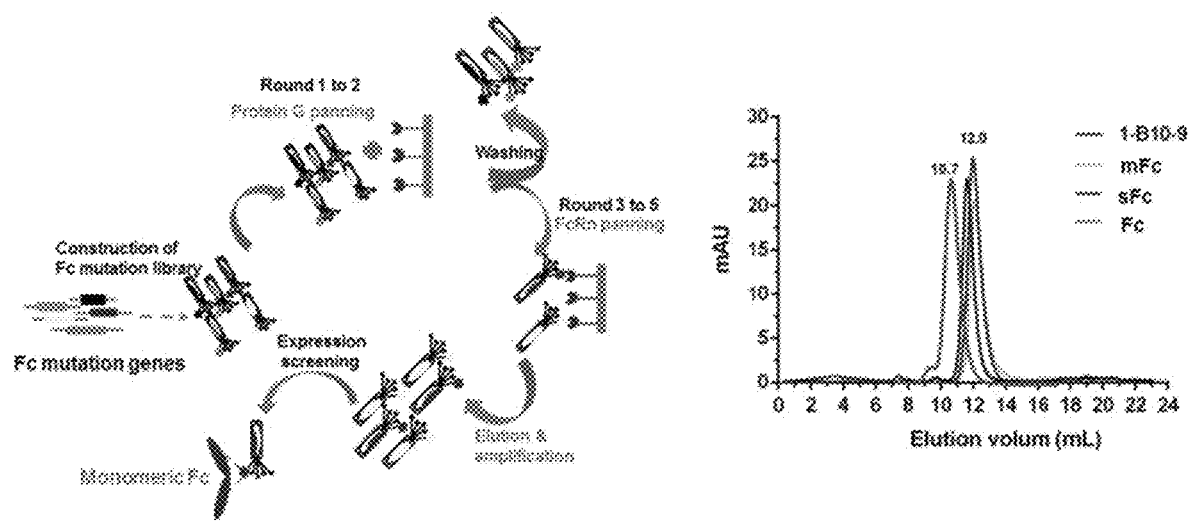
FIG. 1 shows comparison of a novel IgG1 Fc monomer (sFc) with the existing monomers Fc (mFc) and IgG1 Fc by using SEC detection.

Screening and judgment of IgG1 Fc monomer (sFc): A novel IgG1 Fc monomer is screened by biotin-labeled soluble FcRn protein. Biotin-labeled soluble FcRn is immobilized on streptavidin-coated magnetic beads. $10^{12}$ phages displayed Fc at room temperature is incubated with protein G at 1st, 2nd round; and respectively incubated with 5, 4, 2 micrograms of FcRn antigen for two hours at 3rd, 4th, and 5th rounds, $10^{12}$ phages are used for each round of screening, and polyclonal phage ELISA is used to detect enrichment of antibodies. Phages and coated proteins are incubated at the 3rd, 4th, and 5th round, and phage-protein binding is detected with anti-phage HRP-coupled antibodies. Based on polyclonal phage ELISA results, a very significant enrichment is obtained after 4th and 5th round of screening. The phages obtained from these two rounds of screening are used to infect TG1 cells, randomly selecting clones for performing monoclonal phage ELISA, thus further sequencing to identify the enriched IgG1 Fc, and SEC is used to perform monomer judgment. The results are shown in FIG. 1, sFc and another screened protein 1-B10-9 (M428L mutation additionally occurs compared with sFc) are monomers.

Figure 2:
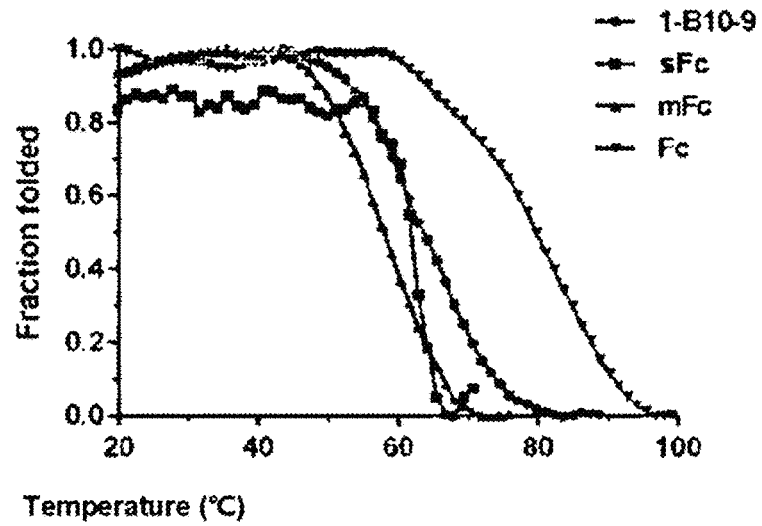
FIG. 2 shows a novel IgG1 Fc monomer stability test.

Novel IgG1 Fc monomer (sFc) stability test: In the present application, sFc, 1-B10-9, mFc and Fc are respectively diluted at a concentration of 0.25 mg/ml, and the stability of the proteins is detected at 216 nm by using the instrument Jasco J-815 spectropolarimeter (Jasco International), and the results are shown in FIG. 2: the Tm values of sFc, 1-B10-9, mFc and Fc are: 62.4±0.1° C., 64.0±0.1° C., 58.4±0.2° C., 80.6±0.3° C.

Figure 3:
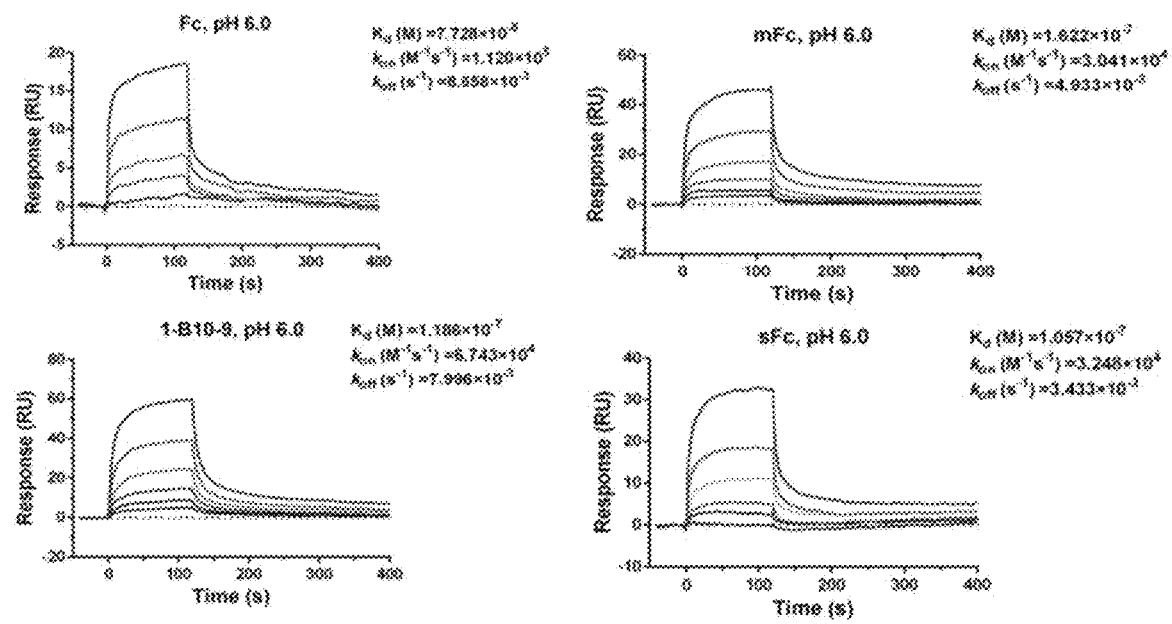
FIG. 3 shows a binding capacity of a novel IgG1 Fc monomer (sFc) to FcRn by surface plasmon resonance (SPR) detection.

Binding capacity of the novel IgG1 Fc monomer (sFc) to FcRn by using surface plasmon resonance (SPR) detection: In the present application, SA (biotin avidin) chip is used to detect the binding capacity of the novel IgG1 Fc monomer to FcRn, wherein the soluble expression preparation of the novel IgG1 Fc monomer is carried out basically based on the literature. During the detection process, the protein is diluted based on a two-fold ratio (IgG1 Fc dilution 200 nM to 6.25 nM, IgG1 Fc monomer dilution 400 nM to 12.5 nM), the affinity constant is detected by detecting binding and dissociation at pH 6.0, the results are shown in FIG. 3: the binding capacity to FcRn of the novel IgG1 Fc monomers sFc or 1-B10-9 remains substantially consistent as compared to Fc or mFc.

Figure 4:
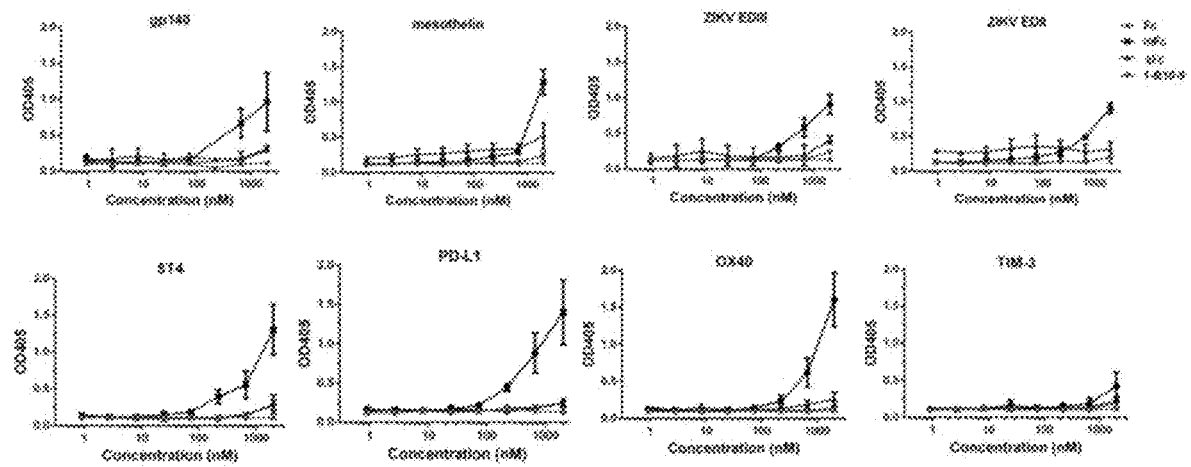
FIG. 4 shows a non-specific detection of a novel IgG1 Fc monomer (sFc) with comparison of the existing monomers Fc (mFc) and IgG1Fc.

Non-specific binding detection of the novel IgG1 Fc monomer (sFc): In the present application, Fc is eukaryotically expressed, mFc and the novel IgG1 Fc monomer sFc are prokaryotically expressed, followed by Protein G purification, and then viruses and cancer-related proteins (gp140, mesothelin, ZIKV EDII, ZIKV EDIII, 5T4, PD-L1, OX40, TIM-3) are used to coat plate (#3690) with 100 ng per well at 4° C. overnight, 100 μl of 3% MPBS (PBS+3% milk) is added into each well, blocking at 37° C. for 1 h, then 0.05% PBST (PBS+0.05% Tween 20) is used for washing, Fc, mFc, novel IgG1 Fc monomer sFc and 1-B10-9 are diluted by 3-fold dilution from 2 μM, incubated with the antigen for 1.5 h at 37° C., washed with 0.05% PBST and added with 1:1000 anti-FLAG-HRP and incubated for 45 minutes at 37° C., and then ABTS is added to develop a color at an absorbance of 405 nm. Comparing their non-specific binding capability, the novel IgG1 Fc monomer is significantly more excellent than mFc. The ELISA results shown in FIG. 4 are that the novel IgG1 Fc monomer sFc and 1-B10-9 have a low non-specific binding.

What is claimed is:

1. An IgG1 Fc monomer polypeptide comprising CH2 and CH3 domains, wherein the polypeptide comprises arginine (R), histidine (H), lysine (K) and threonine (T) at positions 366, 368, 395 and 409 of IgG1, respectively, wherein the numbering is according to EU numbering and the Fc monomer polypeptide is capable of binding to a neonatal Fc receptor (FcRn), wherein the binding affinity of the IgG1 Fc monomer polypeptide to at least one antigen selected from the group consisting of 5T4, PD-L1 and OX40 is lower than that of a wild-type IgG1 Fc, as measured by an enzyme-linked immunosorbent assay (ELISA) with 100 ng of the antigen and up to 223 nM of the IgG1 Fc monomer polypeptide.

2. The IgG1 Fc monomer polypeptide according to claim 1, further comprising an amino acid substitution at position 428 of IgG1.

3. A fusion protein, comprising the IgG1 Fc monomer polypeptide according to claim 1 and a heterologous protein.

4. The fusion protein of claim 3, wherein the IgG1 Fc monomer polypeptide further comprises methionine (M) at position 428 of IgG1.

5. The fusion protein of claim 3, wherein the heterologous protein comprises a heavy chain variable region and a light chain variable region and the heterologous protein is capable of specifically binding to an antigen of interest; the heterologous protein is an antigen, a cytokine, a soluble receptor, a growth factor, a label, a human interferon, an erythropoietin, a soluble tumor necrosis factor receptor, CTLA-4, a soluble IL-4 receptor or a factor I; or the fusion protein comprises a toxin.

6. The fusion protein of claim 3, wherein the heterologous protein is a cytokine.

7. The fusion protein of claim 4, wherein the heterologous protein is a cytokine.

8. An IgG1 Fc monomer polypeptide comprising CH2 and CH3 domains, wherein the CH3 domain comprises the amino acid sequence having residues 111 to 217 of SEQ ID NO: 2, which correspond to positions 341 to 447 of IgG1 according to EU numbering, wherein the binding affinity of the IgG1 Fc monomer polypeptide to at least one antigen selected from the group consisting of 5T4, PD-L1 and OX40 is lower than that of a wild-type IgG1 Fc, as measured by an enzyme-linked immunosorbent assay (ELISA) with 100 ng of the antigen and up to 223 nM of the IgG1 Fc monomer polypeptide.

9. A fusion protein, comprising the IgG1 Fc monomer polypeptide according to claim 8 and a heterologous protein.

10. The fusion protein of claim 9, wherein the heterologous protein comprises a heavy chain variable region and a light chain variable region and the heterologous protein is capable of specifically binding to an antigen of interest; the heterologous protein is an antigen, a cytokine, a soluble receptor, a growth factor, a label, a human interferon, an erythropoietin, a soluble tumor necrosis factor receptor, CTLA-4, a soluble IL-4 receptor or a factor I; or the fusion protein comprises a toxin.

11. An IgG1 Fc monomer polypeptide comprising the amino acid sequence of SEQ ID NO: 2.

12. A fusion protein, comprising the IgG1 Fc monomer polypeptide according to claim 11 and a heterologous protein.

13. The fusion protein of claim 12, wherein the heterologous protein comprises a heavy chain variable region and a light chain variable region and the heterologous protein is capable of specifically binding to an antigen of interest; the heterologous protein is an antigen, a cytokine, a soluble receptor, a growth factor, a label, a human interferon, an erythropoietin, a soluble tumor necrosis factor receptor, CTLA-4, a soluble IL-4 receptor or a factor I; or the fusion protein comprises a toxin.

\* \* \* \* \*

SEQUENCE LISTING

<160> NUMBER OF SEQ ID NOS: 2

<210> SEQ ID NO 1
<211> LENGTH: 217
<212> TYPE: PRT
<213> ORGANISM: Artificial Sequence
<220> FEATURE:
<223> OTHER INFORMATION: Constant region Fc of Antibody
<220> FEATURE:
<221> NAME/KEY: MUTAGEN
<222> LOCATION: (136)..(136)
<223> OTHER INFORMATION: Xaa=Arg/Thr
<220> FEATURE:
<221> NAME/KEY: MUTAGEN
<222> LOCATION: (138)..(138)
<223> OTHER INFORMATION: Xaa=Leu/His
<220> FEATURE:
<221> NAME/KEY: MUTAGEN
<222> LOCATION: (165)..(165)
<223> OTHER INFORMATION: Xaa=Pro/Lys
<220> FEATURE:
<221> NAME/KEY: MUTAGEN
<222> LOCATION: (179)..(179)
<223> OTHER INFORMATION: Xaa=Lys/Thr

<400> SEQUENCE: 1

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Xaa Cys Xaa Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Xaa Pro Val Leu Asp Ser Asp Gly Ser Phe Phe Leu
                165                 170                 175

Tyr Ser Xaa Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 2
<211> LENGTH: 217
<212> TYPE: PRT
<213> ORGANISM: Artificial Sequence
<220> FEATURE:
<223> OTHER INFORMATION: Constnt region Fc of antibody
<220> FEATURE:
<221> NAME/KEY: MUTAGEN

```
<222> LOCATION: (136)..(136)
<223> OTHER INFORMATION: Xaa=Arg
<220> FEATURE:
<221> NAME/KEY: MUTAGEN
<222> LOCATION: (138)..(138)
<223> OTHER INFORMATION: Xaa=His
<220> FEATURE:
<221> NAME/KEY: MUTAGEN
<222> LOCATION: (165)..(165)
<223> OTHER INFORMATION: Xaa=Lys
<220> FEATURE:
<221> NAME/KEY: MUTAGEN
<222> LOCATION: (179)..(179)
<223> OTHER INFORMATION: Xaa=Thr

<400> SEQUENCE: 2

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Arg Cys His Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Lys Pro Val Leu Asp Ser Asp Gly Ser Phe Phe Leu
                165                 170                 175

Tyr Ser Thr Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```